(12) United States Patent
Wotton, III (10) Patent No.: US 9,962,208 B2
(45) Date of Patent: May 8, 2018

(54) BONE ANCHOR (71) Applicant: Harold M Wotton, III, Woodstock, CT (US)

(72) Inventor: Harold M Wotton, III, Woodstock, CT (US)

(73) Assignee: Steris Instrument Management Services, INC., Mentor, OH (US)

( * ) Notice: Subject to any disclaimer, the term of this patent is extended or adjusted under 35 U.S.C. 154(b) by 361 days.

(21) Appl. No.: 14/442,887

(22) PCT Filed: Nov. 13, 2013

(86) PCT No.: PCT/GB2013/052986
§ 371 (c)(1),
(2) Date: May 14, 2015

(87) PCT Pub. No.: WO2014/076470
PCT Pub. Date: May 22, 2014

(65) Prior Publication Data
US 2015/0289917 A1 Oct. 15, 2015

(30) Foreign Application Priority Data
Nov. 14, 2012 (GB) .................................. 1220498.8

(51) Int. Cl.
A61B 17/86 (2006.01)
A61B 17/04 (2006.01)
A61B 17/06 (2006.01)

(52) U.S. Cl.
CPC ........ *A61B 17/864* (2013.01); *A61B 17/0401* (2013.01); *A61B 17/861* (2013.01);
(Continued)

(58) Field of Classification Search
CPC .............. A61B 17/864; A61B 17/0401; A61B 2017/0414; A61B 2017/044; A61B 2017/0496
See application file for complete search history.

(56) References Cited

U.S. PATENT DOCUMENTS 4,773,421 A * 9/1988 Davis ................. A61B 17/0466
24/71.1
6,096,060 A * 8/2000 Fitts ................... A61B 17/0401
606/232

(Continued)

FOREIGN PATENT DOCUMENTS

EP 2319438 5/2011
WO WO 2008/131369 10/2008
(Continued)

OTHER PUBLICATIONS

Communication under Rule 71(3) EPC, EPO, Jul. 7, 2016.*

*Primary Examiner* — Christian Sevilla
(74) *Attorney, Agent, or Firm* — Diederiks & Whitelaw, PLC (57) ABSTRACT A bone anchor for limiting the separation of two bones, for example in a canine knee, comprises a head having a socket for engaging a tool and a shaft extending from the head to a tip. The shaft comprises a threaded section, an intermediate section located between the head and the threaded section and an aperture extending through the intermediate section. The head has a larger diameter than the intermediate section. Also disclosed is a kit of parts comprising two bone anchors and a looped suture and a method for limiting the separation of two parts.

20 Claims, 5 Drawing Sheets (52) U.S. Cl.
    CPC ... *A61B 17/06166* (2013.01); *A61B 2017/044* (2013.01); *A61B 2017/0414* (2013.01); *A61B 2017/0496* (2013.01)

(56) References Cited

U.S. PATENT DOCUMENTS

| | | | |
|---|---|---|---|
| 6,267,766 B1 * | 7/2001 | Burkhart | A61B 17/0401 606/232 |
| 6,540,750 B2 | 4/2003 | Burkhart | |
| 6,569,188 B2 | 5/2003 | Grafton et al. | |
| 7,442,202 B2 | 10/2008 | Dreyfuss | |
| 8,025,677 B2 | 9/2011 | Freid et al. | |
| 2002/0143364 A1 | 10/2002 | Burkhart | |
| 2004/0039404 A1 | 2/2004 | Dreyfuss | |
| 2004/0082954 A1 | 4/2004 | Teitelbaum et al. | |
| 2005/0090827 A1 * | 4/2005 | Gedebou | A61B 17/0401 606/232 |
| 2007/0005068 A1 | 1/2007 | Sklar | |
| 2007/0142861 A1 | 6/2007 | Burkhart | |
| 2007/0173845 A1 * | 7/2007 | Kim | A61B 17/0401 606/232 |
| 2007/0213730 A1 * | 9/2007 | Martinek | A61B 17/0401 606/326 |
| 2008/0086138 A1 * | 4/2008 | Stone | A61B 17/0401 606/265 |
| 2009/0018581 A1 * | 1/2009 | Anderson | A61B 17/0401 606/232 |
| 2009/0318961 A1 * | 12/2009 | Stone | A61B 17/0401 606/228 |
| 2010/0305610 A1 * | 12/2010 | Kim | A61B 17/0401 606/232 |
| 2012/0035671 A1 * | 2/2012 | Hodge | A61B 17/0401 606/328 |
| 2012/0130430 A1 | 5/2012 | Le Roux et al. | |

FOREIGN PATENT DOCUMENTS

| | | |
|---|---|---|
| WO | WO 2010/062379 | 6/2010 |
| WO | WO 2010/123835 | 10/2010 |

* cited by examiner

BONE ANCHOR

CROSS-REFERENCE TO RELATED APPLICATIONS

This application represents a National Stage application of PCT/GB2013/052986 entitled "Bone Anchor" filed Nov. 11, 2013, pending.

BACKGROUND OF THE INVENTION

The present invention relates to an apparatus and method for limiting the separation of two parts, such as two bones.

In particular, the apparatus can be used to stabilise a knee of an animal such as a canine (i.e. a dog). It may be used to stabilise a canine knee that is cruciate deficient, for example, due to a tear in the cranial cruciate ligament (CCL) (analogous to the anterior cruciate ligament (ACL) in humans).

Cranial cruciate ligament deficiency is the most common orthopaedic condition seen in dogs. In a known operation, first and second bone anchors are secured to opposing ends of the tibia and the femur and a suture secured between the two bone anchors. The suture limits the separation of the two bones and thus takes the place, or supplements the role, of the CCL.

Traditionally, the suture is first tensioned and then tied off or crimped. This can be problematic as the suture can wear prematurely at the site of the crimp or the knot. Wear of the suture can lead to failure of the assembly. Another problem with the prior art is that expensive tensioning and crimping assemblies are often required. Yet another problem with prior art bone anchors is that a suture attached to the bone anchor can become worn due to contact with the bone to which the anchor is secured. Yet another problem is the inconsistent results from user to user when using a crimp or tying a knot. Yet another problem is all currently sutures being used are not continuous and the junction created by the knot or crimp is the week point in the fixation.

SUMMARY OF THE INVENTION

The present invention seeks to solve the problems associated with the apparatus and method of the prior art.

In accordance with a first aspect of the present invention, there is provided a bone anchor comprising a head having means for engaging a tool and a shaft extending from the head to a tip, the shaft comprising a threaded section, an intermediate section located between the head and the threaded section, the head having a larger diameter than the intermediate section, and an aperture extending through the intermediate section.

In use, a first looped end of a suture can be passed through the aperture and back over the head, so that the loop is wrapped around the intermediate section. As the head has a larger diameter than the intermediate section, it will retain the looped end of the suture on the shaft. As such, the bone anchor of this aspect of the present invention can retain a suture without any need for a knot or a crimp.

When used with another bone anchor, a continuous loop suture can be used. A second looped end of the suture can be wrapped over a head of a second bone anchor. The continuous loop suture can then be tensioned, to limit the separation of the two bones, by winding the suture around the intermediate section of the first bone anchor. This can be done by rotating the first bone anchor, so that it is screwed into (or further into) a bone of an animal, such as a dog. Winding the suture around the first bone anchor shortens the length of suture extending between the first and second bone anchors and thus places this length of suture under tension. As such, the suture can be tensioned easily and precisely (via small rotations of the first bone anchor) without any need for a separate, expensive tensioning assembly.

The diameters of the intermediate section and the head (and any other part of the bone anchor) in any aspect or embodiment of the present invention, are measured in a radial direction which is perpendicular to a longitudinal axis along which the shaft extends. The threads of the threaded section extend around the longitudinal axis, such that the bone anchor rotates about the longitudinal axis when it is being screwed into a bone. If the diameter of the intermediate section and/or the head varies along its length, the diameter of the head section should be measured at its widest point and the diameter of the intermediate section should be measured at its narrowest point.

The tool may be any tool that can engage the head and rotate the bone anchor so that it is screwed into a bone.

The aperture may take any form as long as it extends through the intermediate section. It need not extend through the longitudinal axis of the shaft, but this may be desirable for ease of manufacture of the bone anchor and to reduce wear on the suture. The aperture may have a circular or non-circular cross-section. Preferably, the walls of the intermediate section defining the aperture present no sharp, raised or protruding edges that would cause wear on the suture.

The aperture may be any size as long as a looped end of a suture can be passed therethrough. The aperture may have a diameter of at least 1.0 mm, or between 1.0 mm and 2.0 mm.

The bone anchor may further comprise a stop extending radially from the intermediate section between the aperture and the threaded section and having a larger diameter than the threaded section. If the diameters of the stop and/or the intermediate section vary along their length, the diameter of the stop and the threaded section should be measured at their widest parts.

The stop serves to prevent the bone anchor being screwed too far into a bone. The stop also protects a suture that passes through the aperture and is looped over the head and around the intermediate section, from contact with the bone and/or the threads. Such contact could cause premature wear of the suture. The suture may therefore be retained on the bone anchor between the head and the stop.

The stop may comprise an annular shelf. In other words, the stop may extend radially from the intermediate section around the whole circumference of the intermediate section.

The stop may have a larger diameter than the intermediate section. This prevents a suture wrapped around the intermediate section from sliding over the stop and contacting the bone and/or the threads. If the diameter of the intermediate section and/or the stop varies along its length, then the diameter of the intermediate section should be measured at its narrowest part and the diameter of the stop should be measured at its widest part.

The stop may be integrally formed with the intermediate section. The intermediate section may be integrally formed with the head and the threaded section.

The intermediate section may comprises no threads. This prevents a suture wrapped around the intermediate section being worn by any threads. The intermediate section preferably comprises one or more smooth surfaces about which a suture can be wound. The smooth surface reduces the wear on the suture.

The intermediate section may have one or more circumferential surfaces. The circumferential extending surfaces provide a smooth, low-wear surface about which a suture can be wound.

The intermediate section has a diameter of at least 2.0 mm, at least 3.0 mm, or between 2.5 mm and 3.5 mm. The Applicant has found, through extensive testing, that depending on the diameter of suture used, there is a minimum diameter of intermediate section about which the suture should be wound to reduce or completely remove any stress risers on the wound suture and therefore, prevent premature failure. It has been found that, when using a suture having a diameter of United States Pharmacopeia (USP) designation of up to 2-0 (0.3 mm), an intermediate section diameter of at least 3.0 mm is required. A smaller diameter of intermediate section can be selected when using a thinner suture, such as 5-0 USP (0.1 mm).

For example, the ratio of the diameter of the intermediate section to the diameter of the flexible material may be at least 8.0, or at least 9.0 or at least 10.0.

The diameter of the head is larger than the diameter of the intermediate section and may be at least 5.0 mm or at least 5.5 mm. The diameter of the head is preferably at least 50%, or at least 75%, greater than that of the intermediate section.

The means for engaging a tool may comprises a hexagonal socket or alike. The hexagonal socket is intended to be engaged by a hexagonal key or driver ('hex-key' or 'Allen-key'®). The key or driver is used to screw the bone anchor into a bone.

The bone anchor may be formed from any suitable implant grade material, such as implant grade stainless steel, titanium or plastic, such as polyether-ether-ketone (PEEK).

The threaded section of the bone anchor may be self-tapping, such that no pre-tapping of holes into the bone is required.

In accordance with a second aspect of the present invention, there is provided a bone anchor comprising a head having means for engaging a tool, a shaft extending from the head to a tip, the shaft comprising a threaded section, an intermediate section located between the head and the threaded section, the head having a larger diameter than the intermediate section, and a stop extending radially from the intermediate section and having a larger diameter than the threaded section.

The stop serves to prevent the bone anchor being screwed too far into a bone. The stop also protects a suture, that is wound around the intermediate section, from contact with the bone and/or the threads. Such contact could cause premature wear of the suture. A suture may be retained on the bone anchor between the head and the stop.

If the diameters of the stop and/or the intermediate section vary along their length, the diameter of the stop and the threaded section should be measured at their widest parts.

The stop may comprise an annular shelf. In other words, the stop may extend radially from the intermediate section around the whole circumference of the intermediate section.

The stop may have a larger diameter than the intermediate section. This prevents a suture wrapped around the intermediate section from sliding over the stop and contacting the bone and/or the threads. If the diameter of the intermediate section and/or the stop varies along its length, then the diameter of the intermediate section should be measured at its narrowest part and the diameter of the stop should be measured at its widest part.

The stop may be integrally formed with the intermediate section. The intermediate section may be integrally formed with the head and the threaded section.

The intermediate section may comprises no threads. This prevents a suture wrapped around the intermediate section being worn by any threads. The intermediate section preferably comprises one or more smooth surfaces about which a suture can be wound. The smooth surface reduces the wear on the suture.

The intermediate section may have one or more circumferential surfaces. The circumferential extending surfaces provide a smooth, low-wear surface about which a suture can be wound.

The intermediate section has a diameter of at least 2.0 mm, at least 3.0 mm, or between 2.5 mm and 3.5 mm. The Applicant has found, through extensive testing, that depending on the diameter of suture used, there is a minimum diameter of intermediate section about which the suture should be wound prevent premature wear. It has been found that, when using a suture having a diameter of United States Pharmacopeia (USP) designation of up to 2-0 (0.3 mm), an intermediate section diameter of at least 3.0 mm is required. A smaller diameter of intermediate section can be selected when using a thinner suture, such as 5-0 USP (0.1 mm).

For example, the ratio of the diameter of the intermediate section to the diameter of the flexible material may be at least 8.0, or at least 9.0 or at least 10.0.

The diameter of the head is larger than the diameter of the intermediate section and may be at least 5.0 mm or at least 5.5 mm. The diameter of the head is preferably at least 50% or at least 75% greater than that of the intermediate section.

The means for engaging a tool may comprises a hexagonal socket or alike. The hexagonal socket is intended to be engaged by a hexagonal key or driver ('hex-key' or 'Allen-key'®). The key or driver is used to screw the bone anchor into a bone.

The bone anchor may be formed from any suitable implant grade material, such as implant grade stainless steel, titanium or plastic, such as polyether-ether-ketone (PEEK).

The threaded section of the bone anchor may be self-tapping, such that no pre-tapping of holes into the bone is required.

The bone anchor may comprise an aperture extending through the intermediate section between the head and the stop. The aperture may have any of the features discussed in relation to any embodiment of the first aspect of the present invention, as discussed above. The aperture allows a first looped end of a suture to be passed through the aperture and back over the head, so that the loop is wrapped over (i.e. encircles) the head. As the head has a larger diameter than the intermediate section, it will retain the looped end of the suture on the shaft.

In accordance with a third aspect of the present invention, there is provided a kit of parts for limiting the separation of first and second bones. The kit of parts comprises a first bone anchor, a second bone anchor and a continuous loop of a flexible material. The first bone anchor may have the features of any of the embodiments of the first and second aspects discussed above. The second bone anchor comprises a head having means for engaging a tool, a shaft extending from the head to a tip, the shaft comprising a threaded section, and an intermediate section located between the head and the threaded section, wherein the head has a larger diameter than the intermediate section.

The continuous loop of a flexible material may be a suture. The suture may be sized such that a first end thereof can be passed through an (or the) aperture of the first bone anchor and back over the head of the first bone anchor, so that the loop is wrapped over (i.e. encircles) the head. As the head has a larger diameter than the intermediate section, it will retain the looped end of the suture on the shaft. The second end of the continuous loop can be passed over the head of the second bone anchor.

The first and second bone anchors can be attached to first and second bones of an animal, such as a dog. The first and second bones may be a tibia and femur or vice versa. The kits of parts may be used to provide a tensile force between two bones such that their separation is limited. The kit of parts may be used to stabilise a cruciate deficient knee or any other joint with ligament damage.

The flexible material may have a diameter of less than 1.0 mm, less than 0.5 mm or between 0.07 mm and 0.35 mm.

The intermediate section of the first bone anchor may have a diameter of at least 2.0 mm, at least 3.0 mm, or between 2.5 mm and 3.5 mm.

The ratio of the diameter of the intermediate section to the diameter of the flexible material may be at least 8.0, at least 9.0, or at least 10.0.

The flexible material may comprise any suitable suture material. The material may be absorbable or non-absorbable (i.e. permanent). The material may be a monofilament. The flexible material may comprise nylon, polyester or an absorbable PGA (polyglycolic acid).

The continuous loop of flexible material may have an unraveled length of up to 8 inches (20.3 cm), up to 7 inches (17.8 cm) or between 2 inches (5.1 cm) and 6 inches (15.2 cm). The unraveled length can be determined by cutting the continuous loop and measuring from one cut end to the other.

The second bone anchor may have the same features as the first bone anchor according to any of the embodiments of the first and second aspects discussed above. However, the aperture will not usually be necessary.

The intermediate section of the second bone anchor may comprise no aperture extending therethrough. The continuous loop can be wrapped around the intermediate section of the second bone anchor so that, in use, it can slide freely around its circumferential surface. If the continuous loop was passed through an aperture in the second bone anchor and over the head (as is the case with the first bone anchor), then it would not be free to slide around the intermediate section. When the first bone anchor is rotated, one side of the loop is pulled towards the first bone anchor, while the other side of the loop becomes slack. It is advantageous for the continuous loop to slide around the second bone anchor as both sides of the loop will then remain under the same tension. This prevents all of the tension acting on one side of the loop at the second bone anchor, which would not utilise the full strength of the loop. As such, preferably, the continuous loop is attached to the second bone anchor in such a way that it can slide freely (in a circumferential direction) around the intermediate section.

The second bone anchor may comprise a stop extending radially from said intermediate section and having a larger diameter than the threaded section.

The intermediate section of the second bone anchor may comprise no threads.

In accordance with a fourth aspect of the present invention, there is provided a tensioning assembly comprising the kit of parts according to any embodiment of the third aspect, as discussed above. The tensioning assembly therefore comprises a first bone anchor, a second bone anchor and a continuous loop of a flexible material. A first end of the continuous loop passes through an or the aperture in the intermediate section of the first bone anchor and loops over the head of the first anchor so that it is retained on the intermediate section by the head. A second end of the continuous loop loops over the head of the second bone anchor so that it is retained on the intermediate section of the second bone anchor by the head.

In use, the first bone anchor may be secured to a first bone, while the second bone anchor may be secured to a second bone. The first and second bones may be a tibia and femur, or vice versa, of an animal such as a dog.

Rotating the first bone anchor causes a portion of the continuous loop to be wound around the intermediate section of the first bone anchor and places the continuous loop extending between the first and second bone anchors under tension. This tension serves to limit the separation of the first and second bone anchors and therefore first and second bones to which they may be attached.

In accordance with a fifth aspect of the present invention, there is provided a method for limiting the separation of first and second parts, the method comprising screwing a first anchor into a first part, screwing a second anchor into a second part, passing a first end of a continuous loop of flexible material through an aperture extending through the first anchor and then over a head of the first anchor so that it is retained thereby, placing a second end of the continuous loop over a head of the second anchor so that it is retained thereby and winding a portion of the continuous loop around the first anchor to place the continuous loop extending between the first and second anchors under tension.

The first and second anchors may have the same features as the first and second bone anchors according to any of the embodiments of any of the first to fourth aspects discussed above.

The continuous loop of flexible material may have the same features as that according to any of the embodiments of any of the first to fourth aspects discussed above. In particular, the continuous loop of flexible material may be a suture.

The first and second ends are looped over the heads of the first and second bone anchors so that they wrap around the intermediate sections thereof. The first and second ends are retained on the intermediate sections of the first and second bone anchors by the heads and, if present, the stops. Preferably, the continuous loop is attached to the second bone anchor in such a way that it can slide freely (in a circumferential direction) around the intermediate section.

Placing the continuous loop extending between the first and second anchors under tension serves to pull the first and second bone anchors towards each other and therefore limit the separation thereof.

The first and second parts may be bones of an animal such as a dog. The bones may be a tibia and a femur.

It should be understood that the first and second anchors can be screwed into the first and second parts, respectively, either before, after or both before and after the flexible material is attached to the first and second anchors.

The step of winding the continuous loop around the first anchor may comprise rotating the first anchor. As discussed above, in relation to the other aspects of the present invention, rotating the first anchor can cause the flexible material to be wound around the intermediate section of the first anchor.

Rotating the first anchor may cause the first anchor to be screwed into, or further into, the first part. In other words, the first anchor may already be partially screwed into the first part before the flexible material is passed through the aperture extending through the first anchor and over the head of the first anchor. Rotating the first anchor further causes the flexible material to be wound around the first anchor as the first anchor is screwed further into the first part. Alternatively, the flexible material may be passed through the aperture and over the head before the first anchor is screwed into the first part at all.

Rotating the first anchor may cause the continuous loop to slide around the intermediate section of the second bone anchor, thus preventing tension acting on one side of the second bone anchor only.

The method may further comprise limiting the amount that the first and/or second anchor are screwed into the first and/or second parts by providing a stop on the first and/or the second anchors. The stop may have the features discussed in relation to any of the embodiments of any of the first to fourth aspects discussed above. The stop serves to prevent the first and/or second anchors being screwed too far into the first and/or second parts and protects the flexible material from contact with the first and/or second parts.

The present invention also extends to a method of stabilising a cruciate deficient knee comprising the method according to the fifth aspect of the present invention and any embodiments thereof.

The present invention also extends to a method of using the kit of parts or tensioning assembly of any embodiment of the third or fourth aspect of the present invention.

The present invention according to each aspect of the present invention may include any or all of the features described in respect of any of the other aspects and embodiments of the invention to the extent that they are not mutually inconsistent therewith.

Although the various aspects of the present invention have been described in relation to bones of a dog, it should be understood that the apparatus and method of the present invention can also be used on the bones of other animals, such as humans. The bone anchors can be used on any bones, and not just the bones in the knee, such as the tibia and femur.

BRIEF DESCRIPTION OF THE DRAWINGS

Some preferred embodiments of the present invention will now be described by way of example only and with reference to FIGS. 1 to 16 of which:

FIGS. 13a to 13d are cross-sectional views of the first bone anchor of FIG. 1 and a continuous loop suture in engagement therewith;

DETAILED DESCRIPTION OF THE INVENTION

FIGS. 1 to 6 show a first bone anchor 10 according to an embodiment of the present invention. The first bone anchor 10 comprises a head 11 having means for engaging a tool, namely a hexagonal socket 18 for engaging a hex-key. The bone anchor 10 can be rotated and screwed into a bone by rotating a hex-key engaged with hexagonal socket 18. The head 11 has a lower rim 11a that defines the widest part of the head 11.

The first bone anchor 10 comprises an intermediate section 12 and a threaded section 13. The intermediate section 12 extends between the head 11 and the threaded section 13. The threaded section 13 extends to tip 14 and comprises screw threads 17. The intermediate section 12 and threaded section 13 form a shaft that extends along longitudinal axis 19.

Figure 3:
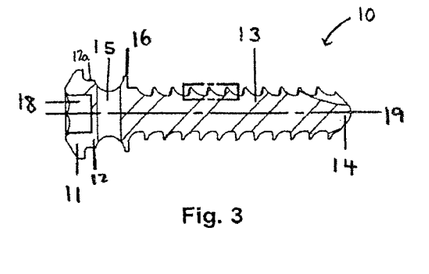
FIG. 3 is cross-sectional view of the bone anchor of FIG. 1 taken along section 3-3 of FIG. 2.
Figure 4:
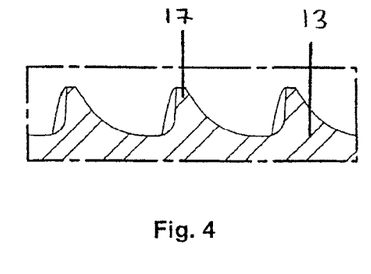
FIG. 4 is an enlarged view of a section of FIG. 3.
Figure 5:
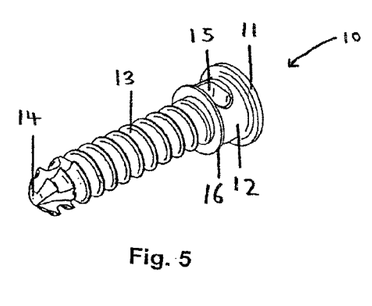
FIG. 5 is a perspective view of the bone anchor of FIG. 1.
Figure 6:
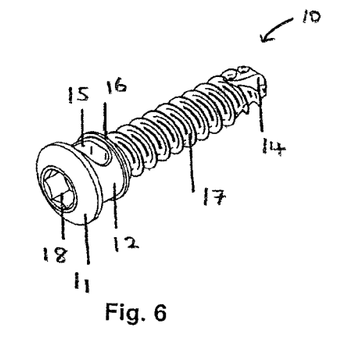
FIG. 6 is another perspective view of the bone anchor of FIG. 1.
Figure 7:
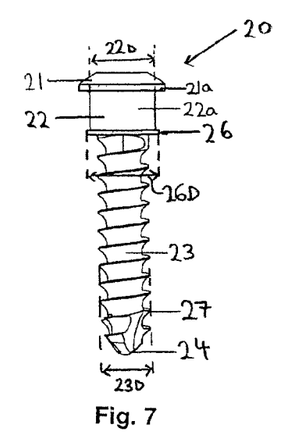
FIG. 7 is a perspective view of a second bone anchor according to one embodiment of the present invention.
Figure 8:
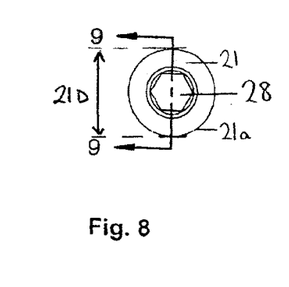
FIG. 8 is a top, plan view of the bone anchor of FIG. 7.

The intermediate section 12 comprises an aperture 15 that extends therethrough. The aperture 15 extends through the longitudinal axis 19 in a radial direction which is perpendicular to the longitudinal axis 19. The aperture 15 in this embodiment has an oval cross-section, but other cross-sectional shapes that provide smooth edges could also be used, such as a circle. The intermediate section 12 has a continuous circumferential surface 12a, through which the aperture 15 extends (both at its entrance and exit). The intermediate section 12 has a diameter $12_D$ that is smaller than the diameter of the head $11_D$ (at the lower rim 11a) (see FIG. 2). The lower rim 11a may therefore prevent a suture that is wound around the intermediate section 12 from slipping over the head 11.

Figure 1:
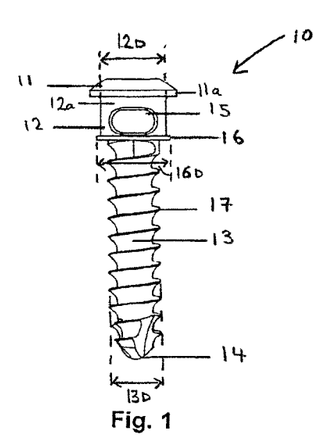
FIG. 1 is a side view of a first bone anchor according to one embodiment of the present invention.
Figure 2:
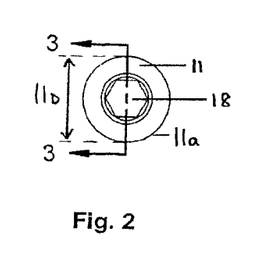
FIG. 2 is a top, plan view of the bone anchor of FIG. 1.

The intermediate section 12 also comprises a radially extending stop 16. The stop 16 is in the form an annular shelf, although other shapes could be used. The stop 16 is located at the top of the threaded section 13 to prevent the intermediate section 12 from being screwed into a bone. The stop 16 has a diameter 16D that is larger than the diameter of the threaded section 13D and the diameter of the intermediate section 12D. This means that the stop 16 can prevent a suture wound around the intermediate section 12D coming into contact with a bone (in which the bone anchor 10 is engaged) and the threads 17.

The first bone anchor 12 of this embodiment is in one-piece, i.e. the head 11, the intermediate section 12, the threaded section 13 and the stop 16 are all integrally formed.

FIGS. 7 to 12 show a second bone anchor 20 according to an embodiment of the present invention. The second bone anchor 20 is identical to the first bone anchor 10 except that there is no aperture passing through the intermediate section 22. The second bone anchor 20 comprises a head 21 having lower rim 21a, an intermediate section 22 having a single, continuous surface 22a, a stop 26 and a threaded section 23 extending to tip 24 and having screw threads 27. The intermediate section 22 and threaded section 23 form a shaft that extends along longitudinal axis 29.

Figure 9:
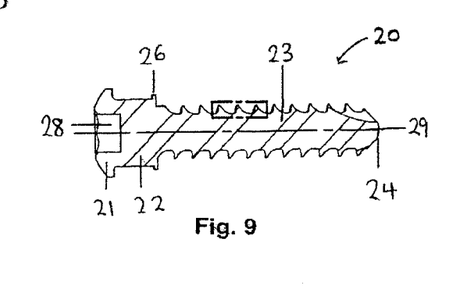
FIG. 9 is cross-sectional view of the bone anchor of FIG. 2 taken along section 9-9 of FIG. 8.
Figure 10:
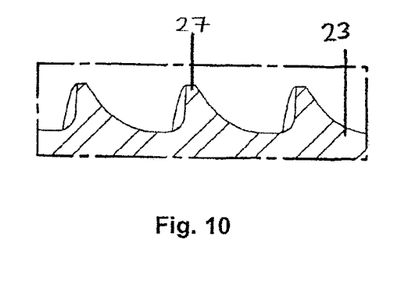
FIG. 10 is an enlarged view of a section of FIG. 9.
Figure 11:
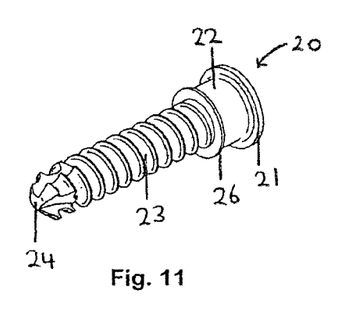
FIG. 11 is a perspective view of the bone anchor of FIG. 7.
Figure 12:
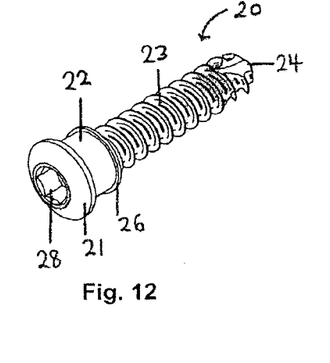
FIG. 12 is another perspective view of the bone anchor of FIG. 7.

The diameter 26D of the stop 26 is larger than the diameter 23D of the threaded section 23 and the diameter 22D of the intermediate section 22. The diameter $22_D$ of the intermediate section 22 is smaller than the diameter of the head 21$_D$ (at the lower rim 21a) (see FIG. 8).

Figure 13A:
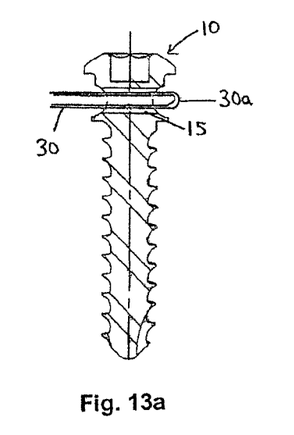
Figure 13B:
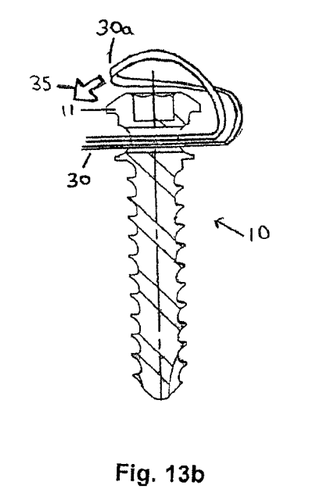
Figure 13C:
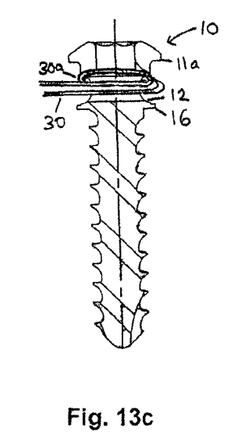

FIGS. 13a to 13c show a continuous loop suture 30 being attached to the first bone anchor 10. In FIG. 13a a first looped end 30a of the suture 30 is passed through the aperture 15 in the first bone anchor 10. As shown in FIG. 13b, the first looped end 30a is pulled through the aperture 15 and over the head 11 in direction 35. The first looped end 30a is then placed around the head 11 so that it wraps around the intermediate section 12. The first looped end 30a is thus retained on the intermediate section 12 by the lower rim 11a of the head 11 and the stop 16.

Figure 14:
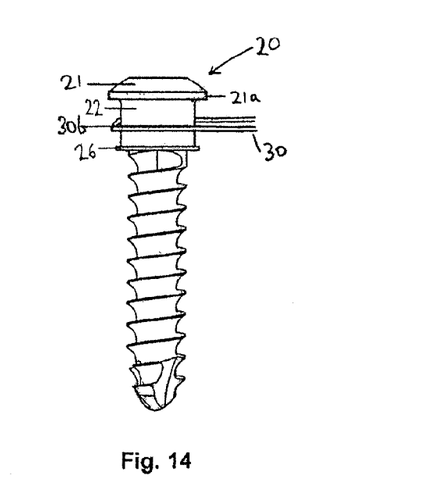
FIG. 14 is a side view of the second bone anchor of FIG. 7 and a continuous loop suture in engagement therewith.

FIG. 14 shows a continuous loop suture 30 attached to the second bone anchor 20. A second looped end 30b of the suture 30 has been passed over and around head 21 so that it wraps around intermediate section 22. The second looped end 30b is retained on the intermediate section 22 by the lower rim 21a of head 21 and the stop 26.

Figure 15:
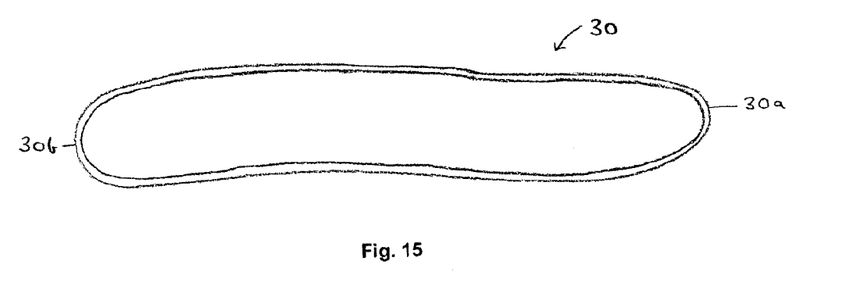
FIG. 15 is a plan view of a continuous loop suture used in methods and apparatus of one embodiment of the present invention.

FIG. 15 shows the continuous loop suture 30 having a first looped end 30a and a second looped end 30b.

Figure 16:
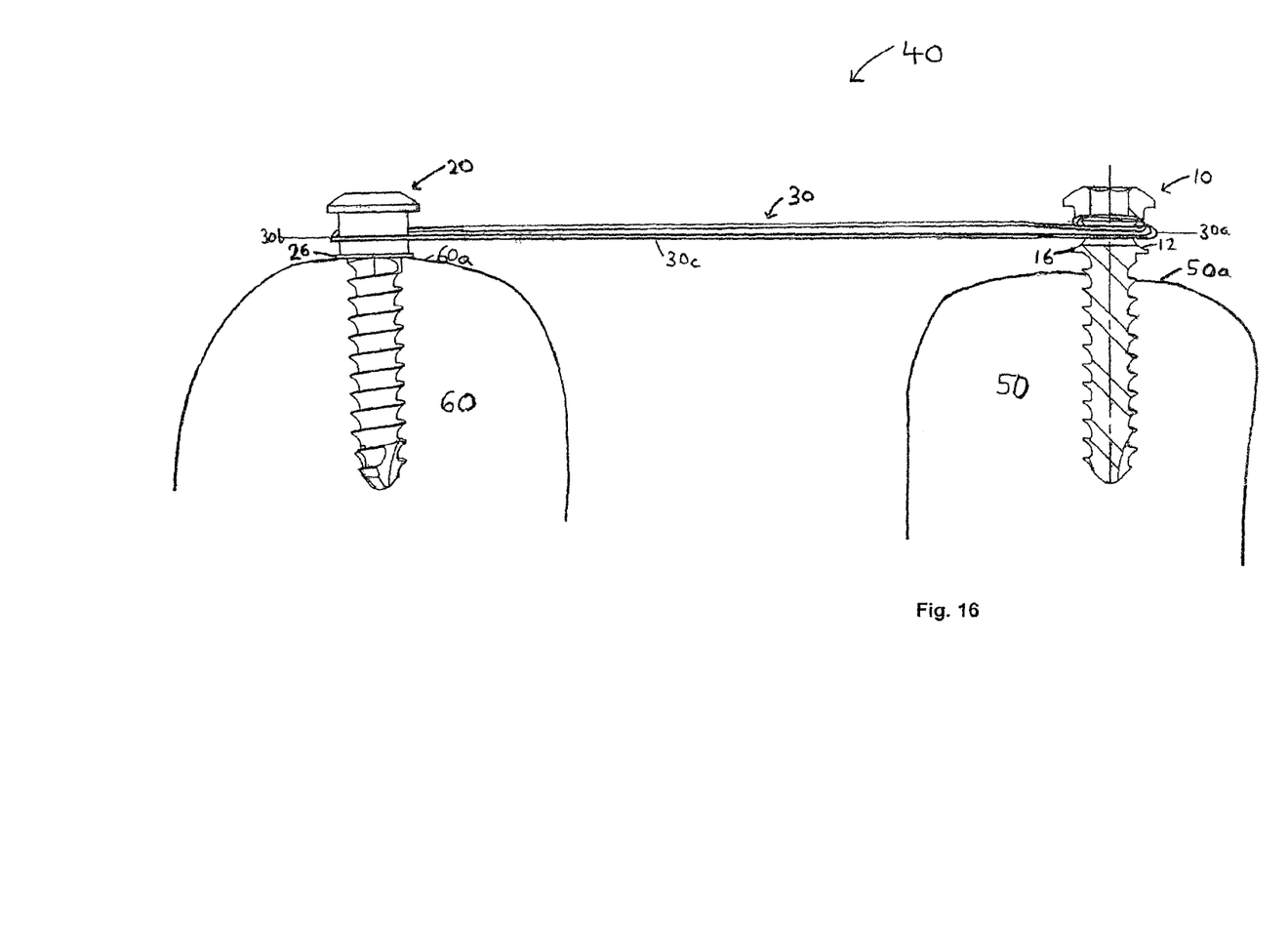
FIG. 16 is a schematic view of an in situ assembly comprising the first and second bone anchors of FIGS. 1 and 7 and the continuous loop suture of FIG. 15 in engagement therewith.

FIG. 16 shows a tensioning assembly 40 comprising the first and second bone anchors 10, 20 and the continuous loop suture 30. The first and second looped ends 30a, 30b of the suture 30 are attached to the first and second bone anchors 10, 20 respectively. For clarity purposes, the side view of the second bone anchor 20 of FIG. 14 is shown, while the cross-sectional view of the first bone anchor 10 of FIG. 13c is shown. The first bone anchor 10 is partially screwed into first bone 50. The second bone anchor 20 is fully screwed into second bone 60, with the stop 26 resting on the upper surface 60a of second bone 60. The first and second bones 50, 60 may be the tibia and femur of an animal, such as a dog.

Screwing the first bone anchor 10 further into the first bone 50 (by rotating the bone anchor 10), causes the continuous loop suture 30 to be wound around the intermediate section 12. The portion 30c of the loop suture 30 that extends between the two bone anchors 10, 20 is then placed under tension. The second looped end 30b of the suture 30 will slide around the intermediate section in the same direction of rotation of the first bone anchor 10, thus equalising the tension on both parts of portion 30c. The tensile force pulls the first and second bones 50, 60 together and thus limits the separation of these bones. The travel of the threaded portion 13 into the bone 50 and thus the rotation of the first bone anchor 10 is limited by the stop 16 meeting the upper surface 50a of the bone 50.

The invention claimed is:

1. A method for limiting the separation of first and second parts, said method comprising:
    screwing a first anchor into a first part;
    screwing a second anchor into a second part;
    passing a first end of a continuous loop of flexible material through an aperture extending through said first anchor and then over a head of said first anchor so that it is retained thereby;
    placing a second end of said continuous loop over a head of said second anchor so that it is retained thereby; and
    winding a portion of said continuous loop around said first anchor to place the continuous loop extending between said first and second anchors under tension, wherein the first and second parts are bones constituted by a tibia and a femur.

2. The method of claim 1, wherein said step of winding said continuous loop around said first anchor comprises rotating said first anchor.

3. The method of claim 2, wherein rotating said first anchor causes said first anchor to be screwed further into said first part.

4. The method of claim 1, further comprising limiting the amount that the first and/or second anchor can be screwed into said first and/or second parts by providing a stop on said first and/or second anchors.

5. A kit of parts for limiting a separation of first and second bones, comprising:
    a first bone anchor comprising:
        a head having means for engaging a tool; and
        a shaft extending from said head to a tip, said shaft comprising:
            a threaded section;
            an intermediate section located between said head and said threaded section, wherein said head has a larger diameter than said intermediate section; and
            an aperture extending through said intermediate section;
    a second bone anchor comprising:
        a head having means for engaging a tool;
        a shaft extending from said head to a tip, said shaft comprising:
            a threaded section; and
            an intermediate section located between said head and said threaded section, wherein said head has a larger diameter than said intermediate section; and
    a continuous loop of a flexible material.

6. The kit of parts of claim 5, wherein said first bone anchor further comprises a stop extending radially from said intermediate section between said aperture and said threaded section and having a larger diameter than said threaded section.

7. The kit of parts of claim 6, wherein said stop:
    comprises an annular shelf;
    has a larger diameter than said intermediate section; and/or
    is integrally formed with said intermediate section.

8. The kit of parts of claim 5, wherein said intermediate section of said first bone anchor has one or more circumferential surfaces.

9. The kit of parts of claim 5, wherein said means for engaging a tool comprises a hexagonal socket.

10. The kit of parts of claim 5 wherein at least one of said first and second bone anchors is formed from stainless steel, titanium or plastic.

11. The kit of parts of claim 5, wherein said threaded section of said first anchor is self-tapping.

12. The kit of parts of claim 5, wherein said flexible material has a diameter of less than 1.0 mm, less than 0.5 mm or between 0.07 mm and 0.35 mm.

13. The kit of parts of claim 5, wherein the intermediate section of said first bone anchor has a diameter of at least 2.0 mm, at least 3.0 mm, or between 2.5 mm and 3.5 mm.

14. The kit of parts of claim 5, wherein the ratio of the diameter of the intermediate section of at least one of said first and second bone anchors to a diameter of the flexible material is at least 8.0, or at least 9.0 or at least 10.0.

15. The kit of parts of claim 5, wherein said flexible material comprises:
    a monofilament; and/or
    nylon, polyester or an absorbable PGA.

16. The kit of parts of claim 5, wherein said second bone anchor comprises a stop extending radially from said intermediate section and having a larger diameter than said threaded section.

17. The kit of parts of claim 5, wherein at least one of the intermediate section of said first bone anchor and the intermediate section of said second bone anchor has no threads.

18. The kit of parts of claim 5, wherein the intermediate section of said second bone anchor has no apertures extending therethrough.

19. A tensioning assembly comprising the kit of parts as claimed claim 5, wherein a first end of said continuous loop passes through said aperture in said intermediate section of said first bone anchor and loops over said head of said first bone anchor so that the first end of said continuous loop is retained on the intermediate section by the head and a second end of said continuous loop loops over said head of said second bone anchor so that the second end of said continuous loop is retained on the intermediate section of the second bone anchor by the head.

20. A tensioning assembly of claim 19, wherein rotating said first bone anchor causes a portion of said continuous loop to be wound around said first bone anchor and places the continuous loop extending between the first and second bone anchors under tension.

\* \* \* \* \*